(12) United States Patent
Huang et al.

(10) Patent No.: US 9,790,535 B2
(45) Date of Patent: Oct. 17, 2017

(54) DISPOSABLE CONTAINER FOR BIOBURDEN SAMPLE COLLECTION AND DETECTION

(71) Applicant: GENERAL ELECTRIC COMPANY, Schenectady, NY (US)

(72) Inventors: Jin Huang, Shanghai (CN); Weimin Xiao, Shanghai (CN); Yan Huang, Shanghai (CN); Chen Luo, Shanghai (CN); Xiaoping Huang, Shanghai (CN); Shukuan Xu, Shanghai (CN); Wenwen Feng, Shanghai (CN); Yan Jin, Shanghai (CN)

(73) Assignee: General Electric Company, Schenectady, NY (US)

( * ) Notice: Subject to any disclaimer, the term of this patent is extended or adjusted under 35 U.S.C. 154(b) by 4 days.

(21) Appl. No.: 14/431,020

(22) PCT Filed: Sep. 25, 2012

(86) PCT No.: PCT/CN2012/081889
§ 371 (c)(1),
(2) Date: Mar. 25, 2015

(87) PCT Pub. No.: WO2014/047770
PCT Pub. Date: Apr. 3, 2014

(65) Prior Publication Data
US 2015/0240284 A1     Aug. 27, 2015

(51) Int. Cl.
*C12Q 1/04*    (2006.01)
*C12Q 1/24*    (2006.01)
(Continued)

(52) U.S. Cl.
CPC ............... *C12Q 1/24* (2013.01); *B01L 3/508* (2013.01); *B01L 3/523* (2013.01); *C12Q 1/04* (2013.01);
(Continued)

(58) Field of Classification Search
None
See application file for complete search history.

(56) References Cited

U.S. PATENT DOCUMENTS 3,295,686 A    1/1967   Krueger
3,929,583 A   12/1975   Sharpe et al.
(Continued)

FOREIGN PATENT DOCUMENTS

CN   101203617 A   6/2008
CN   101755198 A   6/2010
(Continued)

OTHER PUBLICATIONS

Millipore, "Cell Culture Solutions: Millicell® Inserts & Sterile Filtration", Product Selection Guide: BS-GEN-08-00989, Nov. 2008, pp. 1-16.*
(Continued)

*Primary Examiner* — Chris R Tate
*Assistant Examiner* — Aaron J Kosar
(74) *Attorney, Agent, or Firm* — Wegman, Hessler & Vanderburg (57) ABSTRACT

A disposable container for collection of microbe containing fluid samples is useful in a variety of microbial detection methods. One end of the container is provided with a lid comprising fluid flow apertures on one surface and a membrane filter (MF) on an opposed surface. Methods are disclosed wherein the container is disposed in a holding assembly with the lid gripped in a separate platform. The
(Continued)

assembly and platform can be displaced relative to each other to separate the lid from the container.

14 Claims, 5 Drawing Sheets

(51) Int. Cl.
*B01L 3/00* (2006.01)
*G01N 1/30* (2006.01)
*G01N 15/14* (2006.01)

(52) U.S. Cl.
CPC ............ *G01N 1/30* (2013.01); *G01N 15/1463* (2013.01); *B01L 2300/042* (2013.01); *B01L 2300/044* (2013.01); *B01L 2300/0672* (2013.01); *B01L 2300/0681* (2013.01); *B01L 2300/0832* (2013.01); *B01L 2300/123* (2013.01)

(56) References Cited

U.S. PATENT DOCUMENTS

| | | |
|---|---|---|
| 4,317,726 A | 3/1982 | Shepel |
| 4,871,662 A | 10/1989 | Rosov |
| 5,202,262 A | 4/1993 | Lemonnier |
| 5,627,042 A | 5/1997 | Hirose et al. |
| 5,811,251 A | 9/1998 | Hirose et al. |
| 6,329,165 B1 | 12/2001 | Chattoraj et al. |
| 6,358,730 B1 | 3/2002 | Kane |
| 6,699,684 B2 | 3/2004 | Ho et al. |
| 7,618,392 B2 | 11/2009 | Martis et al. |
| 2002/0127630 A1 | 9/2002 | DiGuiseppi et al. |
| 2008/0153125 A1 | 6/2008 | Buttry et al. |
| 2008/0176273 A1 | 7/2008 | Eden et al. |
| 2010/0216183 A1 | 8/2010 | Okanojo et al. |
| 2010/0297691 A1 | 11/2010 | Ribeiro et al. |
| 2012/0021422 A1 | 1/2012 | Spence et al. |

FOREIGN PATENT DOCUMENTS

| | | |
|---|---|---|
| CN | 202047070 U | 11/2011 |
| EP | 1089800 A1 | 4/2001 |
| JP | 2006112875 A | 4/2006 |

OTHER PUBLICATIONS

Ehrlich, R. "Technique for microscopic count of microorganisms directly on membrane filters." Jour Bact (1955) vol. 70, No. 3, pp. 265-268 (STN abstract only).*

European Search Report and Written Opinion issued in connection with corresponding EP Application No. 12885481.7 on Apr. 25, 2016, 6 pages.

Unofficial English Translation of Chinese Office Action issued in connection with corresponding CN Application No. 201280076011.7 on Sep. 30, 2015, 14 pages.

International Search Report and Written Opinion dated Jul. 11, 2013 which was issued in connection with PCT Patent Application No. PCT/CN2012/081889 which was filed on Sep. 25, 2012, 12 pages.

"Rapid Micro Biosystems Announces the 2013 Availability of Growth Direct™ Systems Environmental Monitoring and Sterility Applications", Rapid Micro Biosystems, Apr. 16, 2012, 3 pages.

"Understanding the Concept of Bioburden", Pharma Exec News, Sep. 28, 2009, 2 pages.

Turton, "Microbial Testing: Bioburden", Biopharm International, Dec. 1, 2001, 2 pages.

Bioburden Testing—The Role of Bioburden Testing in Evaluating Healthcare Products, WuXi AppTec , www.wuxiapptec.com, LT228-10-12.06.10.

* cited by examiner

DISPOSABLE CONTAINER FOR BIOBURDEN SAMPLE COLLECTION AND DETECTION

FIELD OF THE INVENTION

The present invention pertains to a disposable container that is useful in the collection and detection of fluid samples containing analyte microbes for a variety of microbial detection methods. Also, the invention relates to microbial measurement methods that are performed using the container as a receptacle for the fluid sample.

BACKGROUND OF THE INVENTION

Bioburden testing has taken an increasingly important role in evaluating the microbial content of a variety of samples in the health care, food, cosmetic, and other industries. Bioburden testing is known by many names including microbial count, viable count, total count, plate count, colony count, heterotrophic count, and mesophilic count. Basically, bioburden is an assessment of the microbiological population associated with a variety of products and components. Obviously, this population is related to cleanliness of raw materials used, the production environment, and the handling of products during various manufacturing stages.

One method of determining microbial counts is a membrane filter (MF) procedure in which microbial counts are determined using a membrane filter. In these MF associated methods, the analyte containing fluid sample is filtered through a MF to capture the desired analyte microbes thereon. In some cases, the captured microbes and MF are placed in contact with a nutrient medium to cultivate the microbes. The number of colonies of microbe containing microbes can be counted using microscopes or cameras.

In some methods, counting of the captured microbes on the MF can be made directly without the need to cultivate the microbes such as by employment of a nutrient medium. In these cases, microscopic or camera detection of the microbes can be made directly by operative association of the detector, such as a microscope or camera with the MF. In many of these direct measurement techniques, the microbes are contacted with a staining or luminescence reagent that reacts with the microbes to facilitate microbe detection.

Accordingly, the present invention is devoted toward a container that can be used to collect the fluid sample and facilitate deposit of the microbes in the sample on a MF for subsequent colony detection by a detection mechanism such as a microscope or camera or the like.

SUMMARY OF THE INVENTION

In one exemplary embodiment, the invention pertains to a disposable container for bioburden sample selection and detection in which the container has a regular clear plastic bottle body, a special structure cap with draining holes at the center area covered by a filtration membrane and sealed by a protective film. The container also has a removable bottom cap with rubber plate.

The system discloses a method in which the container functions as a normal bottle with cap for selecting the water sample. In one embodiment, the container may be placed upside down on a stage or platform assembly connected with a draining pump during the sample preparation process. The container is positioned and secured by a clamping mechanism on the platform which holds the special cap of the container. By turning on the pump, the water sample in the container will be drained out through the filtration membrane and the draining holes on the special cap to the waste. The bacteria of the sample will be left on the filtration membrane and the pump is turned off. A needle mechanism is pointed down through the rubber plate on the bottom cap and injects staining or other reagent into the container. The reagent is drained out by the standard staining process.

After sample preparation process, the container will be moved to another stage with the same clamping mechanism for holding the special cap. Another mechanism will remove the bottle body and the bottom cap but the special cap with filtration membrane will be left on the platform, and the membrane is facing upwardly. A microscope mechanism will be positioned close to the membrane for detection process. After the process is completed, the disposable container can be discharged from the analytical system.

In one embodiment, a sample container is provided for microbial detection processes. The container has a top opening and an opposed bottom opening. A top cap seals the top opening with the top cap comprising a sealing lid including a recessed lid portion. This recessed lid portion comprises a multiplicity of fluid flow apertures therein. A membrane filtration (MF) layer underlies the flow apertures on one side of the recessed lid. A bottom cap assembly seals the bottom opening of the container.

In other exemplary embodiments, the bottom cap assembly comprises an outer cap member and a fluid impervious elastomeric layer underlying the outer cap. The elastomeric layer is penetrable by a needle syringe or other sharp object.

In another aspect of the invention, the top cap comprises a protective film layer overlying the sealing lid. In further embodiments, the sealing lid comprises an annular raised land area surrounding the recessed lid portion. The recessed lid portion may comprise a generally planar surface.

In further embodiments of the invention, the container comprises a cylindrically cross sectioned body member and a neck portion having a smaller diameter than the body portion. Further, a tapered section is provided, in certain embodiments, intermediate the body portion and the neck portion. In certain embodiments, the tapered section has a cross section similar to a truncated cone. The top cap is detachably fit over the neck portion, and the bottom cap assembly is detachably fit over the bottom opening.

Other aspects of the invention pertain to methods for detecting microbial presence in a fluid sample. In certain embodiments, at least a portion of the collection bottle is filled with a fluid sample containing desired analyte microbes therein. A first cap member is provided on one of the openings of the container with this first cap having a first surface comprising fluid flow apertures therein and a membrane filter (MF) layer underlying said first surface. A second cap member is provided on the other of the openings in the container with the second cap member comprising a fluid impervious but needle penetratable surface. The fluid sample is drained through the first cap member, thereby depositing analyte microbes on the MF layer of the first cap. A reagent is injected into the fluid sample through the fluid impervious, needle penetrable second cap surface. The reagent is adapted to react with the analyte microbes in the fluid sample to form a detectable presence on the MF layer. A detector is placed in operative association with the MF layer to detect the presence of analyte microbes on the MF layer.

In certain embodiments of the invention, the reagent comprises a staining agent or, in certain instances, the reagent comprises a luminescent agent adapted to yield luminescent microbes on the MF layer. The detector may, in certain instances, be a microscope or a camera or the like. Additionally, the detector may be CCD (cooled solid state camera device) having an optical detection element that can be inserted into the MF directly.

In further embodiments of the invention, the collection bottle is placed in a bottle holding assembly. After the reagent has been injected into the fluid sample, the first cap member is separated from the collection bottle. In certain embodiments, the first cap member is disposed in a gripping member carried by a platform. The platform and the holding assembly are displaced relative to each other, such as by twisting or the like, to thereby separate the first cap member from the collection bottle. In other embodiments of the invention, a fluid conduit is connected to the first cap member, and the fluid sample is drained through the first cap member and into the fluid conduit. A vacuum or pump means can be attached to the conduit to provide a draining, vacuum source through the conduit to help ensure complete and prompt fluid draining through the cap member and its associated MF layer.

The invention will be further described in conjunction with the appended drawings wherein:

DETAILED DESCRIPTION

Figure 1:
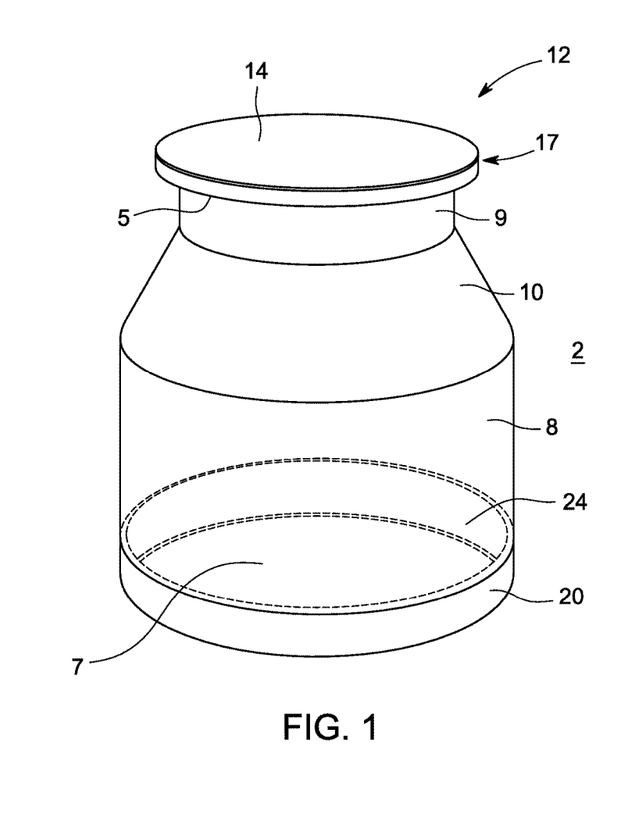
FIG. 1 is a side elevation view of a bioburden sample selection and detection container with certain parts shown in phantom.
Figure 2:
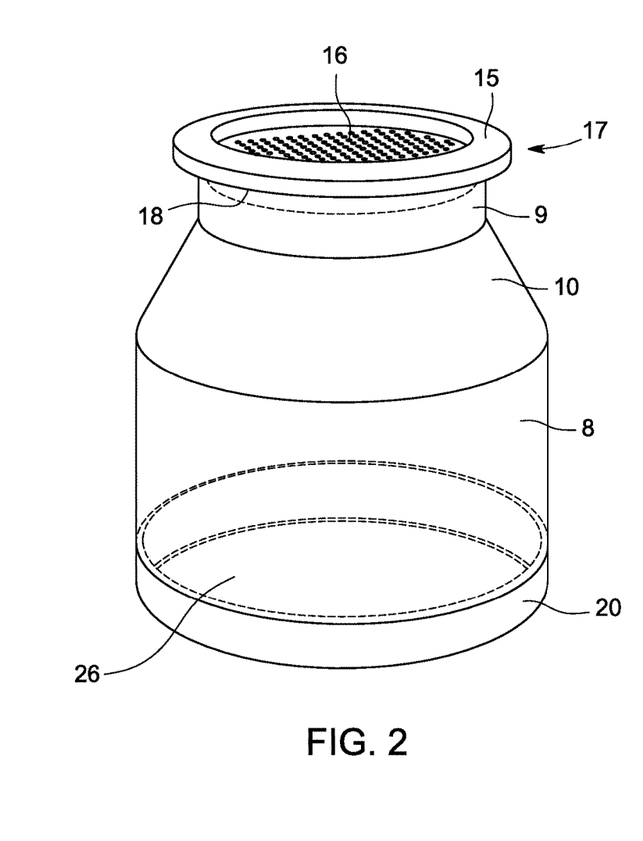
FIG. 2 is a side elevation view of the container of FIG. 1 with the protective film removed from the top cap.
Figure 3:
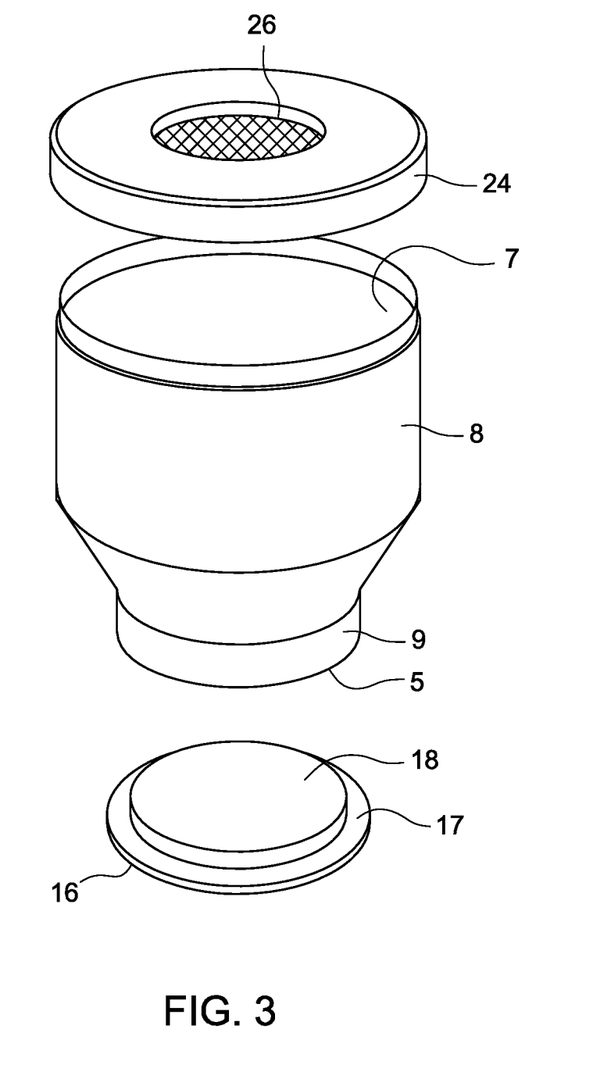
FIG. 3 is an exploded side view of the container with certain parts of the container removed.

Turning to FIGS. 1-3, there is shown a disposable container 2 for bioburden sample selection and detection. The container is composed of a clear plastic material such as polycarbonate, polyethyleneterephlate, polypropylene, or other plastic material. As shown, the container comprises cylindrically cross sectioned body section 8 and a tapered or decreasing diameter section 10 in the general form of a truncated conical shape superposed over the body 8. As shown in FIG. 1, the top most section of the container is defined by a narrowed neck portion 9 over which the cap sections are adapted for engagement by threaded engagement, snap fit, or other like attachment means. With specific reference to FIG. 1, a protective film 14 is provided on the top of the container and is, for example, shrink fit over the top of the container for easy removal. The top cap 12 also includes an annular sealing lid portion 17. The top cap assembly fits over and seals top opening 5 of the container.

At the bottom end of container 2, a removable cap 20 is provided over the bottom or base of the bottle. A fluid impervious rubber diaphragm 26 or similar surface is provided along the inside lower extremity of the bottle, and this may be secured to the bottom of the bottle via sealing cap 24 that can be threaded or snap fit over the bottle base. The cap 20 seals the bottom opening 7 of the container.

In FIG. 2, the protective film 14 has been removed from the top cap 12 revealing annular sealing lid 17 that, in turn, is more particularly friction fit within the circumference of the neck 9. Annular sealing lid 17 comprises a raised annular land area surrounding a recessed, planar section having a multiplicity of apertures 16 therein to facilitate fluid flow through sealing lid 17. On the underneath or bottom side of lid 17 is a filtration membrane 18 that may be composed of polyester, polycarbonate, polypropylene, polytetrafluoroethylene, nylon, and poly(vinylidene difluoride). This membrane functions to retain the microbial species thereon as shall be referred to in detail later.

FIG. 3 shows the container in inverted disposition. This is the orientation in which, in one embodiment, the bottle will be positioned in order to facilitate bioburden sampling and detection. Here, removable outer cap 20 has been removed, revealing the annular securing cap 24 and underlying fluid impenetrable rubber layer 26. The layer 26 is adapted to act as a barrier to fluid flow therethrough, but this layer may be penetrated by a sharp object such as a hypodermic needle or the like. More particularly, layer 26 is formed of an elastomeric material such as EPDM rubber, styrene butadiene, acrylonitrile/butadiene, polychloroprene, or natural rubber. Also, in FIG. 3, the protective film 14 has been removed from the now inverted top of the bottle, revealing filtration membrane 18 on the bottom side of annular snap lid 17 with the recessed aperture side 16 of lid now disposed under the filtration membrane 18.

In order to perform bioburden testing, the bottle 2 is filled with aqueous or other fluid sample containing the analyte microbial species. The bottle 2 may be placed in a bottle holding assembly 100 such as the type shown in FIG. 4. Here, assembly 100 comprises two opposed platen members 102, 104, with the top platen 102 joined to platen 104 via connectors 106, 108, 110, 112 which can all be adjusted through the spring tension supplied by coil spring 114 and 116. A retainer member 120 such as composed of a rubber diaphragm or similar resilient material depends downwardly from the platen 102 and has a general shape that is congruent to the shape of bottle 2 to securely grasp and hold same in the assembly 100.

Figure 4:
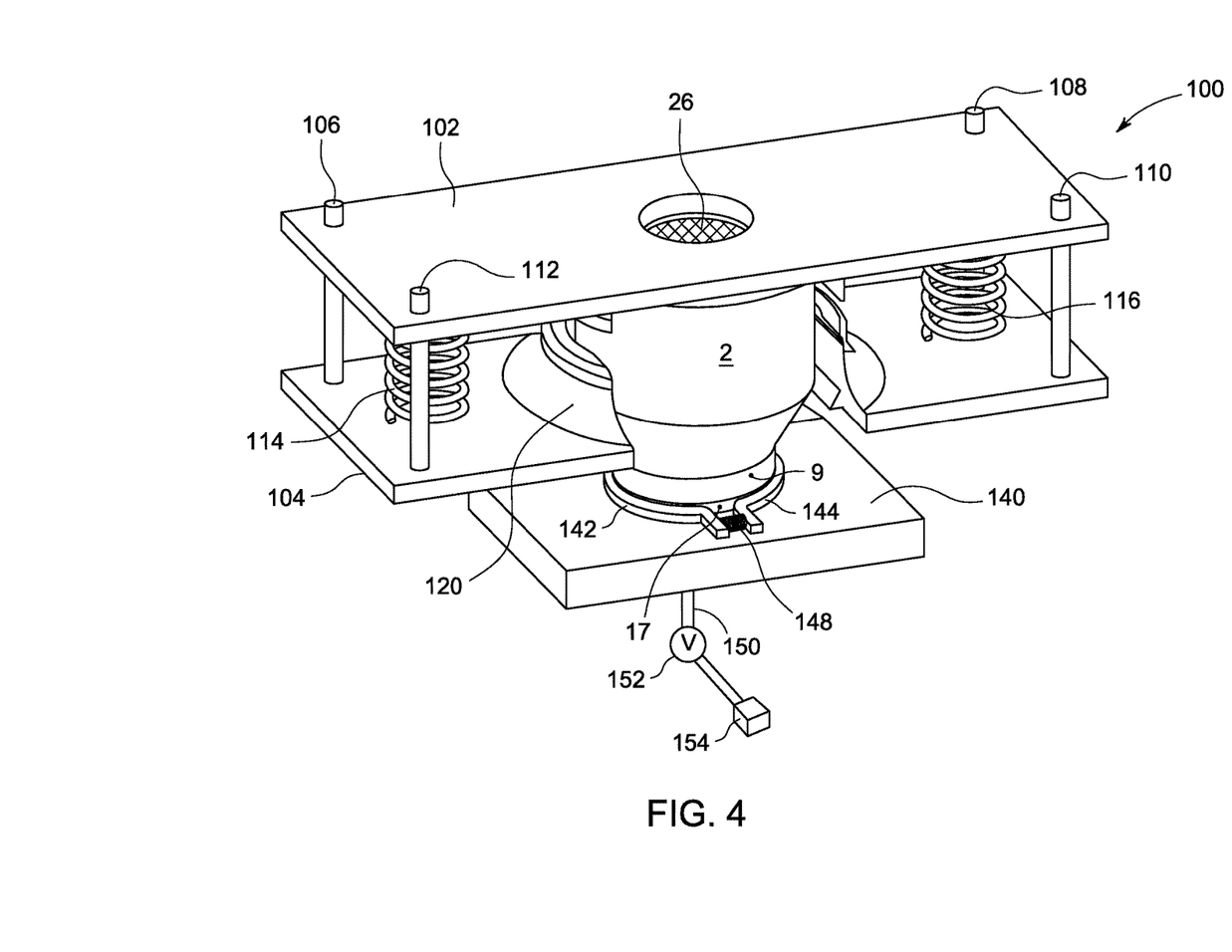
FIG. 4 is a partially cut-away orthogonal projectional view of the container, associated holding assembly and platform during the drainage stage in which fluid is evacuated from the container.

As shown in FIG. 4, platform 140 is positioned underneath the platen 104 and the annular sealing lid 17 is engaged between yoke members 142, 144 carried on the platform, which together, encircle the lid 17. Set screws or the like may be used to vary the tension of springs 146, 148 to provide for secure grasping of lid 17 by the yoke members. At this point, the protective film 14 has been removed from the tap 12, so that the membrane 18 (FIG. 3) is in direct fluid communication with the contents of the bottle 2. A conduit 150 is connected via a funneling type connector or other device (not shown) to the now inverted top section of the bottle. A vacuum source 154 or pump communicates with the bottle 2 via the provision of valve member 152. A hypodermic rubber needle or the like is inserted through the penetratable rubber layer of the bottle to inject staining, luminescence, cleaning, or other reagent or purified water to the fluid sample within bottle 2.

By turning on the vacuum or pump, the fluid in the sample is drained out through the filtration membrane 18 and the draining aperture 16 on the lid 17 to waste. Due to the pore size of the filter membrane, the microbial species of the sample will be captured on the filtration membrane 18, and then the pump or vacuum source is turned off. Thus, after draining the fluid from the bottle, the microbial species and reagent are disposed on the membrane 18 so that the microbial count may then be made via conventional techniques.

Figure 5:
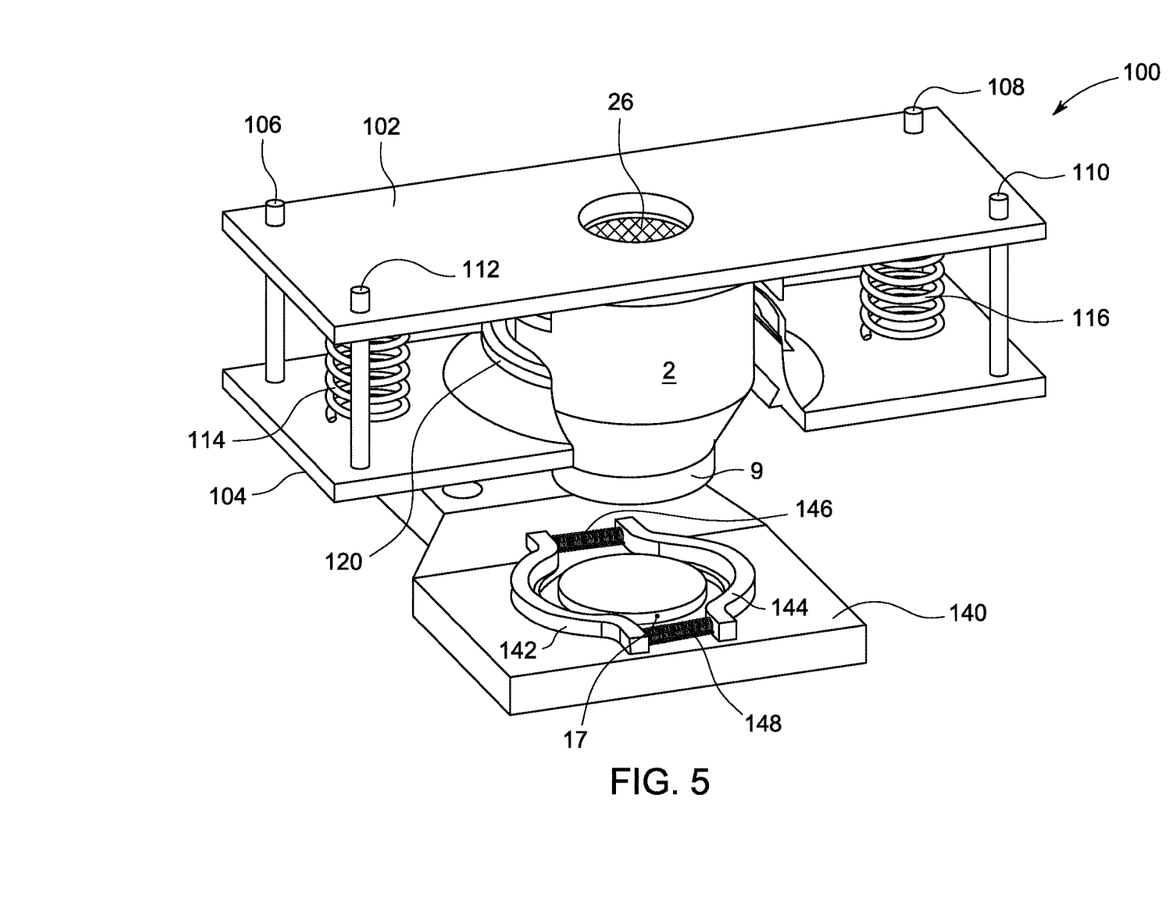
FIG. 5 is a partially cut-away view similar to FIG. 4 but showing another stage in the bioburden testing process in which the platform carrying the membrane filter (MF) is separated from the container holding assembly.

Turning to FIG. 5, as shown, the platform 140 has been removed from the lower platen 104 with the microbial species and reagent disposed on the surface 18. Immediately prior to this step, the lid 17 has been removed from the remainder of the container, leaving lid 17 disposed on the platform. As shown in FIG. 5, the spring tension in springs 146 and 148 has been relaxed with the lid 17 loosely encircled by the yoke members 142, 144. At this stage, a detector such as a microscope or the like can be moved close to the membrane to count or otherwise detect the analyte microbial species. After the inspection, the bottle 2 may be disposed of.

It is thus apparent that a disposable container for bioburden sample selection and detection is provided. This container works as a normal bottle to select the fluid sample and is sealed by a cap. In one aspect of the invention, the container is then placed upside down on stages for sample preparation (filtration, staining) and detection (imaging).

The bioburden measurement process may involve any one of many conventional techniques such as a colorimetric measurement technique in which a staining reagent is injected into the fluid sample in container 2 via a syringe or the like that penetrates the layer 26. A microscope or the like is used to count the microbial colonies on the membrane 18 to assess bioburden level.

Additionally, another exemplary bioburden test method may comprise injection of a luminescent or fluorescent reagent into the sample in the container 2 through the penetrable layer 24. The desired analyte microbial species captured on the surface of membrane 18 can then be detected via a camera or the like placed proximate the membrane 18.

Another bioburden testing procedures that may be utilized involves the "in situ cell division" method. This method is a direct growth rapid method for living target cell detection before the cells become visible to the naked eye. In this method, the sample is filtered through the MF to capture the microorganism thereon. The MF is transferred to a nutrient agar plate and the target cells are allowed to form microcolonies by in situ respiration. (This usually takes about a three-hour incubation time.) The microcolonies are illuminated with a blue light LED (Ex 450-500 nm, Em 510-560 nm). A CCD chip is used to detect cellular autofluorescence and analysis software is used to automatically count the photosensitive pixels overlying each microcolony.

Another exemplary bioburden test procedure is known as the "solid phase cytometry (SPC) method". This method is a rapid method for detection of total viable cells (TVC) by the sequential steps of: (a) filtering a sample over a black polyester or polycarbonate MF to capture microorganisms; (b) transferring the MF to a pad comprising fluorocarbon dye, incubating, to label metabolically active cells only; (c) detecting fluorescence emitted by labeled cells with argon laser scanning (Ex 480 nm, Em 515 nm); (d) processing signals by computer to differentiate valid signals from fluorescent particles; and (e) quantifying total viable cells.

The pore size of the filter membrane is chosen to capture the secured microbial analyte thereon. This pore size can vary over a wide range such as to encompass pore sizes from about 0.05 µm to about 0.65 µm. Exemplary membrane filters (MF) include the following: 1) 25 mm diameter, 7-20 µm thickness, 0.4 µm pore size; 2) 25 mm diameter, 6-11 µm thickness, 0.2 µm pore size; and 3) 47 mm diameter, 7-22 µm thickness, 0.45 µm pore size. The selection of the appropriate filter membrane 18 is within the skill of the artisan.

The artisan will appreciate that bioburden testing can be conducted to determine presence and count levels of a variety of microbes. For example, counts of a variety of bacteria, fungi, mold, yeast, and spores can be conducted using the container and methods of the present invention.

It is to be understood that the invention is not limited to the illustrations described and shown herein, which are deemed to be merely illustrative of various embodiments of the invention and which are suitable for a variety of modifications. The invention is intended to encompass all such modifications which are in the spirit and scope as defined in the attached claims.

What is claimed is:

1. A method of detecting microbial presence in a fluid sample, the method comprising:
   filling at least a portion of a collection bottle with a fluid sample containing analyte microbes therein, said collection bottle comprising opposed top and bottom openings with at least one of said openings being sealed during said filling step;
   providing a first cap member on one opening of said openings, said first cap member comprising a first surface comprising fluid flow apertures therein and a membrane filter (MF) layer underlying said first surface;
   providing a second cap member on another opening of said openings, said second cap member comprising a fluid impervious needle penetrable surface;
   draining said fluid sample through said first cap member thereby depositing said analyte microbes on said MF layer;
   injecting a reagent into said fluid sample through said fluid impervious needle penetrable surface, said reagent configured to react with said analyte microbes to form a detectable presence on said MF layer, said reagent comprising a staining reagent or a luminescent agent configured to yield luminescent microbes on said MF layer; and
   placing a detector in operative association with said MF layer to detect said analyte microbes.

2. The method as recited in claim 1, wherein said detector is a microscope.

3. The method as recited in claim 1, wherein said detector comprises a camera.

4. The method as recited in claim 1, further comprising placing said collection bottle in a bottle holding assembly, and after said step of injecting said reagent into said fluid sample, separating said first cap member from said collection bottle.

5. The method as recited in claim 4, further comprising securing said first cap member in a gripping member carried by a platform, wherein said platform and said bottle holding assembly are displaced relative to each other to thereby separate said first cap member from said collection bottle.

6. The method recited in claim 1, further comprising connecting a fluid conduit to said first cap member, and draining said fluid sample through said fluid conduit.

7. The method as recited in claim 6, further comprising applying a vacuum source to said fluid conduit.

8. A method of detecting microbial presence in a fluid sample, the method comprising:
   filling at least a portion of a collection bottle with a fluid sample containing analyte microbes therein, said collection bottle comprising opposed top and bottom openings with at least one of said openings being sealed during said filling step;

providing a first cap member on one opening of said openings, said first cap member comprising a first surface comprising fluid flow apertures therein and a membrane filter (MF) layer underlying said first surface;

providing a second cap member on another opening of said openings, said second cap member comprising a fluid impervious needle penetrable surface;

draining said fluid sample through said first cap member thereby depositing said analyte microbes on said MF layer; and placing a detector in operative association with said MF layer to detect said analyte microbes.

9. The method as recited in claim 8, wherein said detector is a microscope.

10. The method as recited in claim 8, wherein said detector comprises a camera.

11. The method as recited in claim 8 further comprising placing said collection bottle in a bottle holding assembly, and separating said first cap member from said collection bottle.

12. The method as recited in claim 11, further comprising securing said first cap member in a gripping member carried by a platform, wherein said platform and said bottle holding assembly are displaced relative to each other to thereby separate said first cap member from said collection bottle.

13. The method recited in claim 8, further comprising connecting a fluid conduit to said first cap member, and draining said fluid sample through said fluid conduit.

14. The method as recited in claim 13, further comprising applying a vacuum source to said fluid conduit.

\* \* \* \* \*